(12) United States Patent
Tsuneishi et al.

(10) Patent No.: US 7,675,623 B2
(45) Date of Patent: Mar. 9, 2010

(54) STANDARD DEVICE FOR ORIGIN OF LIGHT ABSORBANCE AND METHOD OF USING THE SAME

(75) Inventors: Shoichi Tsuneishi, Nagaokakyo (JP); Satoru Kohno, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 12/199,048

(22) Filed: Aug. 27, 2008

(65) Prior Publication Data
US 2009/0231585 A1    Sep. 17, 2009

(30) Foreign Application Priority Data
Mar. 12, 2008    (JP)    ............... 2008-063182

(51) Int. Cl.
*G01N 21/00* (2006.01)
*G01N 21/47* (2006.01)
*G01J 1/10* (2006.01)
*A61B 5/00* (2006.01)

(52) U.S. Cl. .................... 356/432; 356/446; 356/243.1; 600/310

(58) Field of Classification Search .................. None
See application file for complete search history.

(56) References Cited
U.S. PATENT DOCUMENTS

| | | | |
|---|---|---|---|
| 4,047,032 A * | 9/1977 | Judge et al. ............... 250/338.5 |
| 4,321,930 A * | 3/1982 | Jobsis et al. ................ 600/344 |
| 5,529,065 A * | 6/1996 | Tsuchiya .................... 600/310 |
| 6,094,265 A * | 7/2000 | Ishikawa et al. ............ 356/244 |
| 6,430,513 B1 * | 8/2002 | Wang et al. ................... 702/28 |
| 6,956,649 B2 * | 10/2005 | Acosta et al. ............. 356/243.1 |
| 7,139,600 B2 * | 11/2006 | Maki et al. .................. 600/344 |
| 2004/0008343 A1 * | 1/2004 | Pawluczyk et al. ....... 356/243.1 |

FOREIGN PATENT DOCUMENTS
JP    05-277118 A    10/1993

OTHER PUBLICATIONS

Aritificial Organs 19(1), 535-538 (1990) Noninvasive Monitoring of Brain Oxygen Metabolism During Cardiopulmonary Bypass by Near Infrared Spectrophotometry (English Abstract attached).
Pediatrics vol. 75 No. 2, 217-225, Feb. 1985 "Noninvasive Monitoring of Cerebral Oxygenation in Preterm Infants: Preliminary Observations".

* cited by examiner

*Primary Examiner*—Tarifur Chowdhury
*Assistant Examiner*—Gordon J Stock, Jr.
(74) *Attorney, Agent, or Firm*—Darby & Darby

(57) ABSTRACT

A device for origin of light absorbance used in an optical measuring instrument for measuring light absorption characteristics of a light diffusion sample. The device includes a light transmission terminal configured to irradiate a measurement light onto the light diffusion sample at a point of incidence of the light diffusion sample and a light diffusion plate through the interior of which the measurement light can be diffused and transmitted. A light receiving terminal is configured to receive the measurement light from the light diffusion sample for measurement at a point of detection of the light diffusion sample that is separate from the point of incidence. Optionally, the device can include a cleaning unit that cleans the light transmission terminal and light receiving terminal.

6 Claims, 5 Drawing Sheets

STANDARD DEVICE FOR ORIGIN OF LIGHT ABSORBANCE AND METHOD OF USING THE SAME

CROSS-REFERENCE TO RELATED APPLICATION

The present application claims priority under 35 U.S.C. §119(a) from Japanese Patent Application No. 2008-063182 filed on Mar. 12, 2008, and is hereby incorporated by reference in its entirety herein.

FIELD OF THE INVENTION

The present invention relates to a standard device for origin of light absorbance and method of using the same used in order to determine the origin of light absorbance in an optical measuring instrument to measure the optical characteristics (for example, changes in light absorbance, etc.) of a light diffusion sample such as a living body, and in particular, relates to a standard device for origin of light absorbance and method of using the same used in order to determine the origin of light absorbance in an optical measuring instrument using light to measure metabolism in a living body (for example, a living body oxygen monitor).

BACKGROUND

Light with a wavelength $\lambda$ of 700 to 1000 nm can pass through the interior of a living body relatively easily compared to light of other wavelengths, and therefore, there have been attempts to use 700 to 1000 nm light to non-invasively measure the fluctuation volumes of hemoglobin, oxygenated hemoglobin, and cytochrome aa3, which have absorption bands of 700 to 1000 nm.

For example, a method (refer, for example, to non-patent literature 1) has been disclosed to obtain the oxygenated hemoglobin fluctuation volume, the reduced hemoglobin fluctuation volume, and the total hemoglobin fluctuation volume based on the light absorbance changes $\Delta A(780)$, $\Delta A(805)$, and $\Delta A(830)$ at various wavelengths $\lambda$ calculated by transmitting 3 types of light, with wavelengths $\lambda$ of 780, 805, and 830 nm, into a living body, and receiving the reflected light and transmitted light from within the living body.

With this kind of measurement method, the light absorbance changes $\Delta A(780)$, $\Delta A(805)$, and $\Delta A(830)$ at various wavelengths $\lambda$ are calculated and the fluctuation volume from a given standard of oxygenated hemoglobin fluctuation volume, etc. is thus obtained. For example, the standard for the measurement of light absorbance changes $\Delta A(780)$, $\Delta A(805)$, and $\Delta A(830)$ is the level of light absorbance, etc. at the time of mounting the optical measuring instrument (for example, an oxygen monitor for a living body, etc.) on the patient (living body), and the level obtained is the amount of change when taking that initial level as the standard. However, no information about the condition of the patient can be obtained at all at the time of mounting the optical measuring instrument on the patient, and therefore, there are the problems that the measurement results from a different day cannot be compared, and that measurement results obtained between different patients cannot be compared.

In order to compare measurement results obtained on a different day or to compare measurement results obtained from different patients, it is necessary to calculate the absolute value $A(\lambda)$ of light absorbance (called "absolute light absorbance" hereinafter) rather than calculating the light absorbance change $\Delta A(\lambda)$ that takes the level of light absorbance at the time of mounting the optical measuring instrument on the patient as the standard. In order to calculate the absolute value $A(\lambda)$, the origin of light absorbance must be set.

When the target of measurement is a chemical substance and not a living body such as a patient, there are the well-known methods of taking a fluid that does not contain any components to be measured (for example, distilled water, etc.) as the origin of light absorbance, or using barium sulfate powder as a standard of 100% reflectivity for measuring fabric and printed material. On the other hand, in order to apply this to an optical measuring instrument that irradiates measurement light on one part of a diffusion material such as a living body, which is the measurement target of the present invention, and detects the measurement light that exits from another part, it is desirable that the origin of light absorbance fulfill the conditions of having the same diffusion transmissivity as the living body, of having the same photosensitivity $T(\lambda)$ as the living body, and also of changing very little over time.

Here, "photosensitivity" $T(\lambda)$ shall be the value calculated by formula (1) below.

$$T(\lambda)=I(\lambda)/Io(\lambda) \qquad (1)$$

$Io(\lambda)$ is the light intensity of the light transmitted, and $I(\lambda)$ is the light intensity of the light received.

Moreover, the "light absorbance" $A(\lambda)$ shall be the value calculated by formula (2) below.

$$A(\lambda)=-\log T(\lambda) \qquad (2)$$

Thus, because the condition of having the same photosensitivity $T(\lambda)$ as the living body is fulfilled, a standard device for origin of light absorbance may be offered that can set the origin of light absorbance (for example, refer to patent literature 1). FIG. 5 indicates a perspective view indicating the configuration of a conventional standard device for origin of light absorbance. In addition, FIG. 4 is a diagram for explaining the measurement method using living body oxygen monitor 26.

This kind of conventional standard device for origin of light absorbance 20 comprises a polyacetal resin plate (light diffusion plate) 3 through the interior of which measurement light can be diffused and transmitted, and a neoprene rubber plate 4 affixed to the back surface of the polyacetal resin plate 3.

Meanwhile, the living body oxygen monitor 26 provides a light transmission light guide 6 for transmitting the measurement light, a light receiving light guide 8 for receiving the measurement light, an operating key 28 for operating the living body oxygen monitor 26, a liquid crystal display panel 30, and a recorder 32. Moreover, a light transmitting unit (light transmission terminal) 7 that irradiates light onto the target for measurement (a living body, standard device for origin of light absorbance) is provided on the end of the light transmission light guide 6; and a light receiving unit (light receiving terminal) 9 that receives measurement light from the target for measurement is provided on the end of the light reception light guide 8.

When setting up the origin of the light absorbance using this kind of standard device for origin of light absorbance 20, the light transmitting unit 7 and the light receiving unit 9 come into contact with the surface of the polyacetal resin plate 3, and the light absorbance $a(\lambda)$ is calculated by using the light receiving unit 9 to detect the measurement light that passes through the interior of the polyacetal resin plate 3. Then, by conducting automatic gain settings, etc. using the living body oxygen monitor 26 main unit, calibration is conducted such that the output of the light absorbance a(λ) is "0" (origin).

As indicated in FIG. 4, when measuring the absolute light absorbance A(λ) of the interior of the brain of the patient using the living body oxygen monitor 26, the light transmitting unit 7 and the light receiving unit 9 come into contact with the surface of the head of the patient, and the change in light absorbance ΔA(λ) from the origin "0" is derived by using the light receiving unit 9 to detect the measurement light that has passed through the brain of the patient. Then, the absolute light absorbance A(λ) is calculated by adding the light absorbance a(λ) to the derived change in light absorbance ΔA(λ).

[Patent literature 1] Japan Unexamined Patent Publication No. H5-277118

[Non-patent literature 1] "Pediatrics" 75, 217-225 (1985), "Artificial Organs" 19, 535-538 (1990).

Nonetheless, as indicated in FIG. 4 for example, when obtaining the absolute light absorbance A(λ) of the brain of the patient, the light transmitting unit 7 and light receiving unit 9 of the living body oxygen monitor contacted the surface of the patients head, but, because contamination such as dandruff or oils and the like on the surface of the head of the patient could adhere to the light transmitting unit 7 and the light receiving unit 9, after the measurement was completed, it was necessary to use a cotton swab or the like immersed in alcohol or the like to remove the contamination adhering to the light transmitting unit 7 and the light receiving unit 9; and this required labor.

In addition, if the contamination adhering to the light transmitting unit 7 and the light receiving unit 9 was not completely removed and the origin of light absorbance was set using the standard device for origin of light absorbance 20, the origin of light absorbance was set while the specified light absorbance still could not be obtained, and errors were included in the measurements as a result.

SUMMARY OF THE INVENTION

An object of the present invention is to provide a standard device for origin of light absorbance that can easily clean the light transmission terminal and light receiving terminal of the optical measuring instrument when setting up the origin of light absorbance.

The standard device for origin of light absorbance of the present invention for resolving the aforementioned problems is a standard device for origin of light absorbance used in an optical measuring instrument, which, with the point of incidence of the measurement light onto a light diffusion sample separate from the point of detection of the measurement light from said light diffusion sample, measures light absorption characteristics of said light diffusion sample; comprising in a single unit a light diffusion plate through the interior of which said measurement light can be diffused and transmitted, and a cleaning unit that cleans the light transmission terminal and light receiving terminal of said optical measuring instrument.

According to the standard device for origin of light absorbance of the present invention, first, contamination adhering to the light transmission terminal and receiving terminal of the optical measuring instrument is eliminated by the cleaning unit when setting up the origin of light absorbance. Then, with the contamination adhering to the light transmission terminal and receiving terminal of the optical measuring instrument removed, measurement light emitted from the light transmission terminal is made to enter into the interior of the light diffusion plate from the surface of the light diffusion plate, pass through the interior of the light diffusion plate, exit to the exterior of the light diffusion plate from the surface of the light diffusion plate, and arrive at the light receiving terminal.

As indicated above, according to the standard device for origin of light absorbance of the present invention, the light transmission terminal and receiving terminal of the optical measuring instrument can be easily cleaned when setting up the origin of light absorbance without preparing a cotton swab or the like immersed in alcohol.

Moreover, when a specified light intensity cannot be obtained by the light receiving terminal, contamination can be easily eliminated by the cleaning unit once again, and therefore, the origin of light absorbance can be set accurately while confirming whether or not the specified light intensity can be obtained by the light receiving terminal. Consequently, even if multiple light transmission terminals and light receiving terminals are combined in the optical measuring instrument, fluctuations caused by combining the light transmission terminals and light receiving terminals can be controlled, and S/N differences caused by combining the light transmission terminals and light receiving terminals can be kept to a minimum.

With the standard device for origin of light absorbance of the present invention, the aforementioned cleaning unit may comprise a cleaning tank formed by side walls such that the surface of said light diffusion plate is taken to be the bottom surface of the tank, and an ultrasonic transducer that generates ultrasonic vibrations in a cleaning solution that has been filled into the interior of the aforementioned cleaning tank.

DETAILED DESCRIPTION OF CERTAIN PREFERRED EMBODIMENTS

Figure 1:
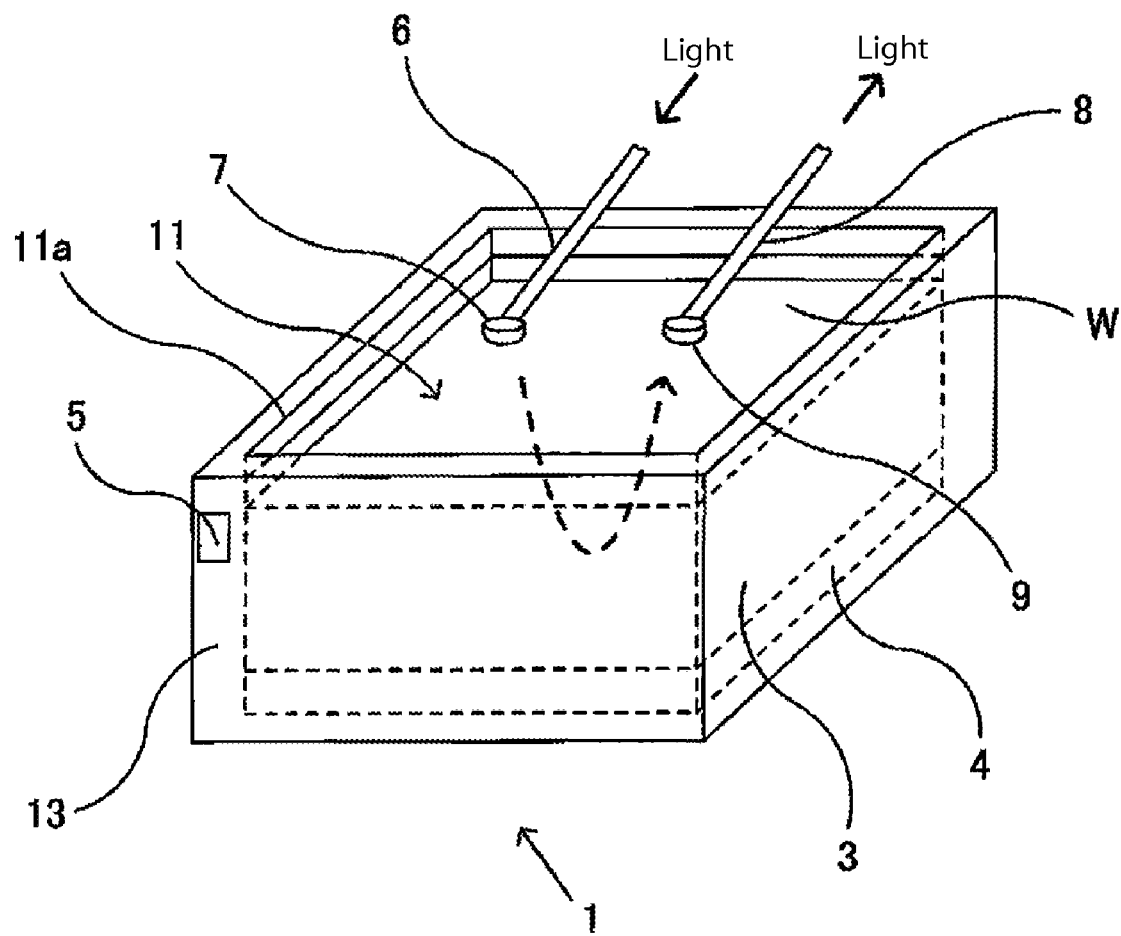
FIG. 1 is a perspective diagram indicating the configuration of a standard device for origin of light absorbance that is an embodiment of the present invention.

According to the present invention, cleaning solution is filled inside a cleaning tank and the light transmission terminal and light receiving terminal are immersed in the cleaning solution. With the light transmission terminal and light receiving terminal immersed in the cleaning solution, ultrasonic vibration of the cleaning solution causes an air bubble crushing phenomenon based on cavitation, and the impact waves associated with this air bubble crushing effectively peel off and crush contamination adhering to the light transmission terminal and the light receiving terminal. Then, after the contamination adhering to the light transmission terminal and the light receiving terminal has been removed, with the light transmission terminal and light receiving terminal remaining immersed in the cleaning solution, the measurement light emitted from the light transmission terminal can be made to enter into the interior of the light diffusion plate from the surface of the light diffusion plate, pass through the interior of the light diffusion plate, exit to the exterior of the light diffusion plate from the surface of the light diffusion plate, and arrive at the light receiving terminal.

As indicated above, according to the present invention, when the specified light intensity cannot be obtained by the light receiving terminal, contamination adhering to the light transmission terminal and the light receiving terminal can be removed just by causing ultrasonic vibration of the cleaning solution once again without requiring movement of the light transmission terminal and the light receiving terminal.

Moreover, with the standard device for origin of light absorbance of the present invention, the aforementioned cleaning unit may be a fabric laminated on the surface of the aforementioned light diffusion plate.

With the standard device for origin of light absorbance of the present invention, a drive mechanism may be comprised to rotate the laminar body of the aforementioned fabric and light diffusion plate such that the direction perpendicular to said fabric and light diffusion plate is the axis of rotation.

According to the present invention, the transmission terminal and the light receiving terminal contact the surface of the fabric. With the transmission terminal and the light receiving terminal contacting the surface of the fabric, contamination adhering to the transmission terminal and the light receiving terminal is removed by rotating the laminar body. Then, after removing the contamination adhering to the transmission terminal and the light receiving terminal of the optical measuring instrument, with the transmission terminal and the light receiving terminal remaining in contact with the surface of the fabric, measurement light emitted from the light transmission terminal is made to enter into the interior of the light diffusion plate from the surface of the light diffusion plate, pass through the interior of the light diffusion plate, exit to the exterior of the light diffusion plate from the surface of the light diffusion plate, and arrive at the light receiving terminal.

As indicated above, according to the present invention, when the specified light intensity cannot be obtained by the light receiving terminal, contamination adhering to the light transmission terminal and the light receiving terminal can be removed just by causing rotation of the laminar body once again without requiring movement of the light transmission terminal and the light receiving terminal.

Then, the method of using a standard device for origin of light absorbance of the present invention used in an optical measuring instrument, which, with the point of incidence of the measurement light onto a light diffusion sample separate from the point of detection of the measurement light from the applicable light diffusion sample, measures light absorption characteristics of the aforementioned light diffusion sample, comprising in a single unit a light diffusion plate through the interior of which the aforementioned measurement light can be diffused and transmitted, and a cleaning unit that cleans the light transmission terminal and light receiving terminal of the aforementioned optical measuring instrument, and the aforementioned cleaning unit comprises a cleaning tank formed by side walls such that the surface of the aforementioned light diffusion plate is taken to be the bottom surface of the tank, and an ultrasonic transducer that generates ultrasonic vibrations in a cleaning solution that has been filled into the interior of the aforementioned cleaning tank, wherein with the light transmission terminal and light receiving terminal immersed in the aforementioned cleaning solution, after contamination adhering to the aforementioned light transmission terminal and light receiving terminal has been removed by causing ultrasonic vibration of the aforementioned cleaning solution, with the light transmission terminal and light receiving terminal remaining immersed in the aforementioned cleaning solution, measurement light emitted from the aforementioned light transmission terminal is made to enter into the interior of the light diffusion plate from the surface of the aforementioned light diffusion plate, pass through the interior of the aforementioned light diffusion plate, exit to the exterior of the light diffusion plate from the surface of the light diffusion plate, and arrive at the aforementioned light receiving terminal.

In addition, the method of using a standard device for origin of light absorbance of the present invention used in an optical measuring instrument, which, with the point of incidence of the measurement light onto a light diffusion sample separate from the point of detection of the measurement light from the aforementioned light diffusion sample, measures light absorption characteristics of the aforementioned light diffusion sample, comprising a light diffusion plate through the interior of which the aforementioned measurement light can be diffused and transmitted, a fabric laminated on the surface of the aforementioned light diffusion plate, and a rotating drive mechanism that causes the laminar body of the aforementioned fabric and light diffusion plate to rotate such that the direction perpendicular to the aforementioned fabric and light diffusion plate is the axis of rotation, wherein, with the light transmission terminal and light receiving terminal contacting the surface of the aforementioned fabric, after contamination adhering to the aforementioned light transmission terminal and light receiving terminal has been removed by causing ultrasonic vibration of the aforementioned cleaning solution, with the light transmission terminal and light receiving terminal remaining in contact with the surface of the aforementioned fabric, measurement light emitted from the aforementioned light transmission terminal is made to enter into the interior of the light diffusion plate from the surface of the aforementioned light diffusion plate, pass through the interior of the aforementioned light diffusion plate, exit to the exterior of the light diffusion plate from the surface of the light diffusion plate, and arrive at the aforementioned light receiving terminal.

Further, in a preferable form of the standard device for origin of light absorbance of the present invention, a light absorption plate is comprised on the back side of the light diffusion plate.

Here, a milk white resin plate, etc. can, for example, be used as the aforementioned light diffusion plate; specifically, polyacetal resin plate (product name: Duracon), polypropylene resin plate, polyethylene tetrafluoride resin plate, or foam styrol resin plate may be used.

Black colored plate and the like can, for example, be used as the aforementioned light absorption body; specifically, black-colored neoprene rubber plate, and black alumite processed aluminum may be used.

Water, alcohol and the like may be used, for example, as the aforementioned cleaning solution.

An ultrasonic oscillator may, for example, be used as the aforementioned ultrasonic transducer; specifically, a device may be used that has a structure in which metal blocks back both ends of a piezoelectric element, and ultrasonic vibration is generated by applying an alternate voltage source to that piezoelectric element.

Embodiments of the present invention will be explained using the diagrams. Further, the present invention is not limited to the following embodiments, and includes a variety of forms within a range that does not deviate from the thrust of the present invention.

Figure 2:
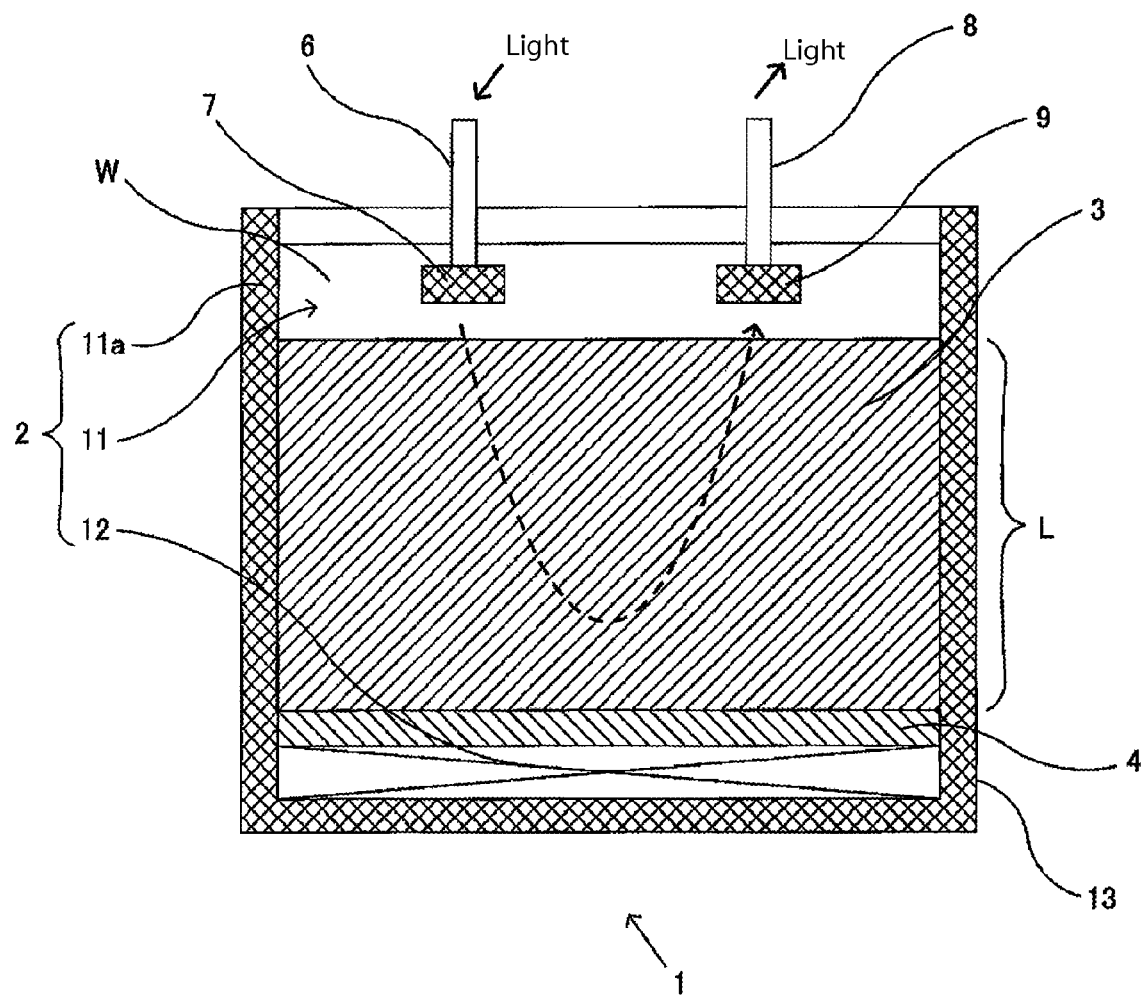
FIG. 2 is a cross-sectional diagram of the standard device for origin of light absorbance indicated in FIG. 1.

FIG. 1 is a perspective drawing indicating the configuration of an embodiment of the present invention. FIG. 2 is a cross-sectional diagram of the standard device for origin of light absorbance indicated in FIG. 1.

The standard device for origin of light absorbance 1 comprises a polyacetal resin plate (light diffusion plate) 3 through the interior of which measurement light can be diffused and transmitted, a neoprene rubber plate (light absorption body) 4 that is affixed to the back side of the polyacetal resin plate 3 and that absorbs the measurement light, and container main body 14 that is open only on the upper surface.

The measurement light can be diffused and transmitted through the interior of the polyacetal resin plate 3, which is formed using Duracon (registered trademark). In addition, approximate dimensions of a length of 50 mm×width of 80 mm×depth of 20 mm are, for example, suitable for the size of the polyacetal resin plate 3.

The neoprene rubber plate 4 is affixed to the back surface of the polyacetal resin plate 3, and absorbs the measurement light. In addition, approximate dimensions of a length of 50 mm×width of 80 mm×depth of 3 mm are, for example, suitable for the size of the neoprene rubber plate 4.

The details will be described later, but when the light transmission unit (light transmission terminal) 7 and the light receiving unit (light receiving terminal) 9, which are from the living body oxygen monitor (light measuring instrument) 26, are contacting the surface of the polyacetal resin plate 3, the measurement light emitted from the light transmission unit 7 enters the interior of the polyacetal resin plate 3 from the surface of the polyacetal resin plate 3, passes through the interior of the polyacetal resin plate 3, and then arrives at the light receiving unit 9 from the surface of the polyacetal resin plate 3.

Here, the thickness L of the polyacetal resin plate 3 is formed to make a preferable absorbency $a(\lambda)$, and if the thickness L is small, the absorbency $a(\lambda)$ becomes large because a large amount of measurement light is absorbed by the neoprene rubber plate 4, and as the thickness L becomes larger, the absorbency $a(\lambda)$ becomes smaller because the affect of the neoprene rubber plate 4 absorbing the measurement light becomes smaller, and finally the absorbency $a(\lambda)$ is determined independently by the polyacetal resin plate 3. Further, a light absorbency $a(\lambda)$ of approximately 5.0 is obtained when the light transmission unit 7 and the light receiving unit 9 are 44 mm apart and come into contact with the surface of the head of a living body; and therefore, with the standard device of origin of light absorbance 1, when the light transmission unit 7 and the light receiving unit 9 are 44 mm apart and come into contact with the surface of the polyacetal resin plate 3, the thickness L of the polyacetal resin plate 3 is formed at 20 mm so that the absorbency $a(\lambda)$ is approximately 5.0.

Further, the thickness of the neoprene rubber plate 4 is not particularly limited.

A container main unit 13 is a receptacle open only on the top, and the interior space is formed to a size large enough to match the polyacetal resin plate 3 and the neoprene rubber plate 4. Approximate dimensions of a length of 50 mm×width of 80 mm×height of 30 mm are, for example, suitable.

Thus configured, when the laminar body, comprising a lamination of the polyacetal resin plate 3 and the neoprene rubber plate 4, is placed in the interior space of the receptacle main unit 13 so that the neoprene plate 4 is to the bottom, a cleaning tank 11 formed by side walls 11a, is formed so that the surface of the polyacetal resin plate 3 comprises the bottom.

Water (cleaning solution) W is filled into the interior of the cleaning tank 11 formed in this way to a height of 5 mm from the bottom (surface of the polyacetal resin plate 3). Further, a water depth (height from the surface of the polyacetal resin plate 3) of 2.5 to 7.5 mm is preferable.

The details will be explained later, but next the light transmission unit 7 and the light receiving unit 9 are immersed in the water W. At this time, it is preferable to immerse in the water W by positioning the light transmission unit 7 and the light receiving unit 9 at a height 2.5 mm from the bottom (surface of the polyacetal resin plate 3), and by having the light transmission unit 7 and the light receiving unit 9 be 44 mm apart. Specifically, it is preferable to set the light transmission unit 7 and the light receiving unit 9 apart at the same interval as that when the light transmission unit 7 and the light receiving unit 9 are mounted on the patient and measurements are taken.

Moreover, an ultrasonic transducer 12 is installed at the bottom of the container main unit 13, and a power source switch 5 of the ultrasonic transducer 12 is installed on the side wall of the container main unit 13.

Then, the irradiation surface of the ultrasonic vibration of the ultrasonic transducer is bonded to the bottom surface of the container main unit 13, and ultrasonic vibration is irradiated such that it advances upward from the irradiation surface. When the power switch 5 is turned ON, an air bubble crushing phenomenon based on cavitation is thereby produced in the water W by causing ultrasonic vibration of the water W, and contamination adhering to the light transmission unit 7 and the light receiving unit 9 arranged in the water W can be peeled off and pulverized by the impact waves associated with this air bubble crushing.

Further, a cleaning unit 2 comprises the cleaning tank 11 and the ultrasonic transducer 12.

Figure 3:
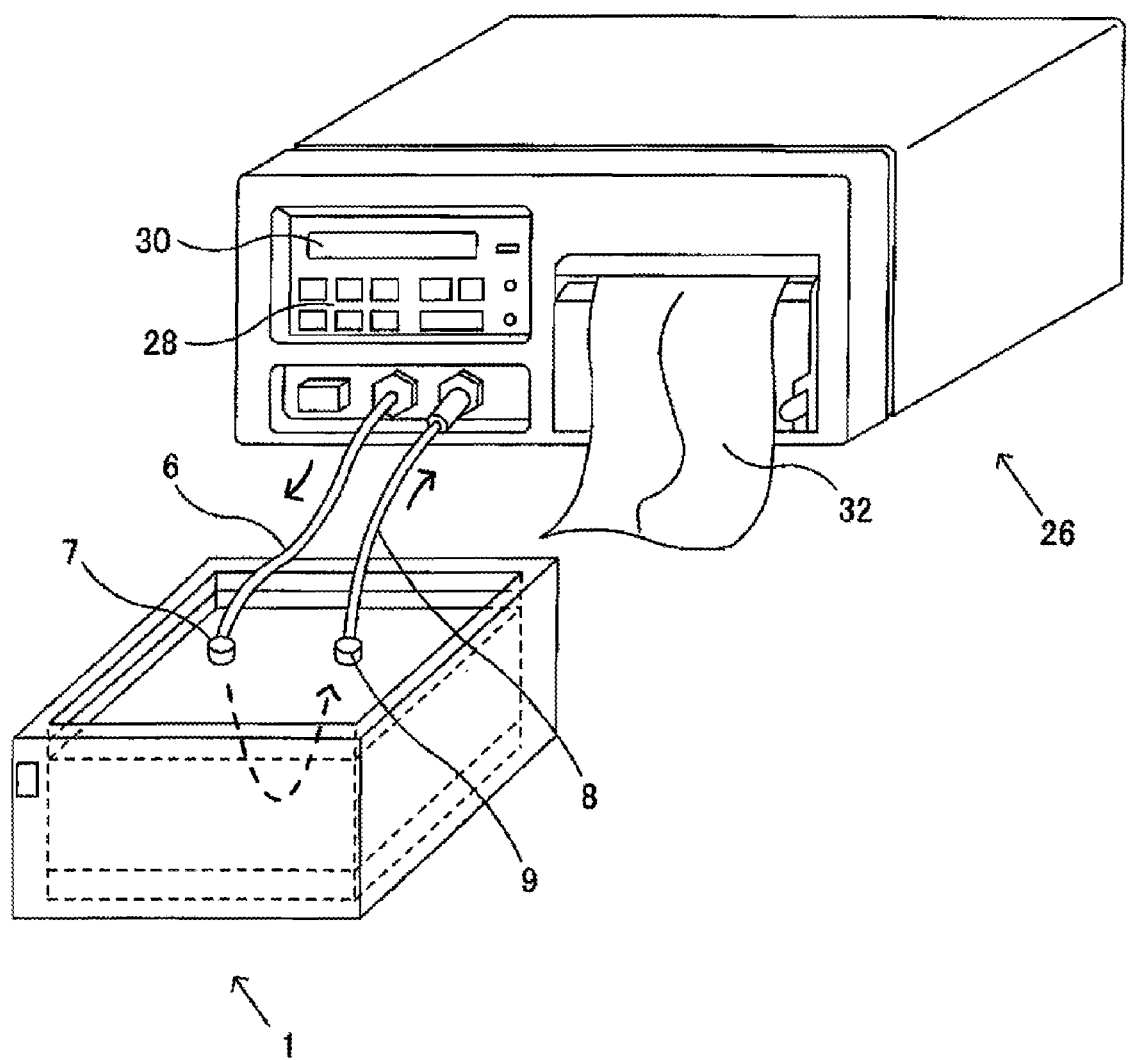
FIG. 3 is a diagram for explaining the method of setting up a standard device for origin of light absorbance.

Next, an example will be explained of a method to set up the origin of light absorbance of the living body oxygen monitor 26 using the standard device for origin of light absorbance 1. FIG. 3 is a diagram for explaining the set-up method based on the standard device for origin of light absorbance 1.

The living body oxygen monitor 26 comprises a light transmission light guide 6 to transmit measurement light, a light receiving light guide 8 to receive the measurement light, a operating key 28 to operate the living body oxygen monitor 26, a liquid crystal display panel 30, and a recorder 32. Moreover, the tip of the light transmission light guide 6 comprises the light transmission unit 7 that irradiates light on the measurement target (living body, standard device for origin of light absorbance 1), and the tip of the light receiving light guide 8 comprises the light receiving unit 9 that receives the measurement light from the measurement target.

Then, when the origin of light absorbance setting up, first, the water W is filled into the cleaning tank 11 of the standard device for origin of light absorbance 1 to make a height of 5 mm from the bottom surface (surface of the polyacetal resin plate 3), and the light transmission unit 7 and the light receiving unit 9 are immersed in the water W. At this time, the light transmission unit 7 and the light receiving unit 9 are immersed in the water W positioned at a height of 2.5 mm from the bottom surface (surface of the polyacetal resin plate 3), and the light transmission unit 7 and the light receiving unit 9 are set 44 mm apart.

Next, with the light transmission unit 7 and the light receiving unit 9 immersed in the water W, the power switch 5 is turned ON, the air bubble crushing phenomenon based on cavitation is generated by causing ultrasonic vibration of the water W, and the contamination adhering to the light transmission unit 7 and the light receiving unit 9 are peeled off and crushed by the impact waves associated with this air bubble crushing.

Then, after the contamination adhering to the light transmission unit 7 and the light receiving unit 9 has been removed, the power switch is turned off, and with the light transmission unit 7 and the light receiving unit 9 remaining immersed in the water W, measurement light emitted from the light transmission terminal 7 enters into the interior of the light diffusion plate 3 from the surface of the light diffusion plate 3, passes through the interior of the light diffusion plate 3, exits to the exterior of the light diffusion plate 3 from the surface of the light diffusion plate 3, and arrives at the light receiving terminal 9.

Next, whether or not the light absorbance $a(\lambda)$ derived in this way enters within the preset range of light absorbance (for example, 3 to 7) is confirmed, and that there are no anomalies in the living body oxygen monitor 26 is verified.

If the specified light intensity cannot be obtained by the light receiving unit 9 at this time, ultrasonic vibration of the water W is conducted once again, and the contamination adhering to the light transmission unit 7 and the light receiving unit 9 is removed. Then, if it can be verified that there are no anomalies with the living body oxygen monitor 26, the light transmission unit 7 and the light receiving unit 9 is taken out from the water W.

Next, calibration is conducted by setting the light absorbance $a(\lambda)$ output to "0" (origin) using the automatic guide setting or the like of the living body oxygen monitor 26. Further, if the absolute light absorbance $A(\lambda)$ is measured using multiple wavelengths $\lambda$, then calibration is conducted respectively by setting those multiple light absorbance $a(\lambda)$ outputs of various wavelengths to "0" (origin).

Figure 4:
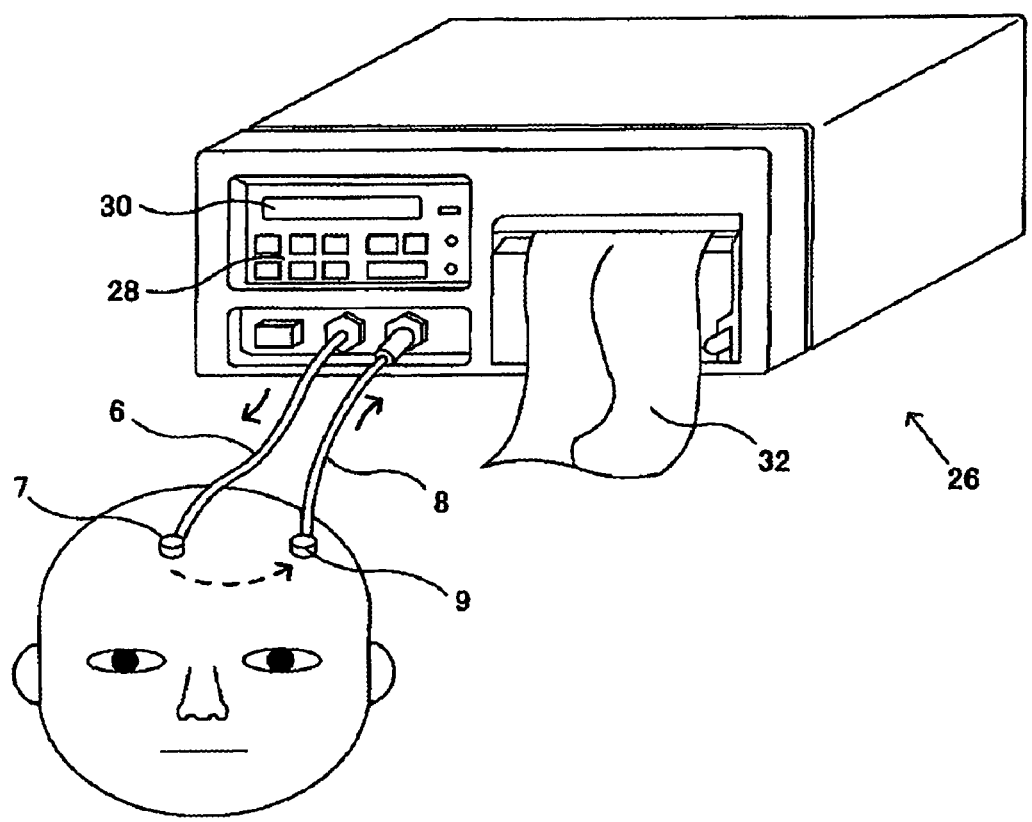
FIG. 4 is a diagram for explaining the method of measuring using a living body oxygen monitor.
Figure 5:
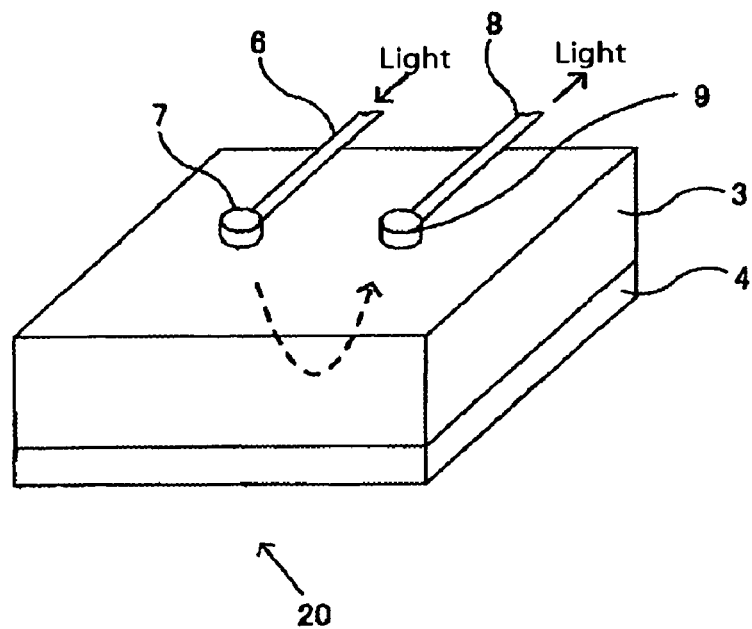
FIG. 5 is a perspective diagram indicating the configuration of a conventional standard device for origin of light absorbance.

Next, an example of the measurement method to measure the brain of the patient using the living body oxygen monitor 26 will be explained (refer to FIG. 4).

First, the light transmission unit 7 and the light receiving unit 9 are mounted on the patient targeted for measurement. At this time, the light transmission unit 7 and the light receiving unit 9 are mounted 44 mm apart. Then, the light absorbance change $\Delta A(\lambda)$ is measured.

Next, the absolute light absorbance $A(\lambda)$ is calculated by adding the light absorbance $a(\lambda)$ to the output of the light absorbance change $\Delta A(\lambda)$ derived in this way. Further, if multiple wavelengths $\lambda$ are measured, the absolute light absorbance $A(\lambda)$ is obtained for each wavelength $\lambda$.

According to the standard device for origin of light absorbance of the present invention described above, when measuring the origin of light absorbance, the light transmission unit 7 and the light receiving unit 9 of the living body oxygen monitor 26 can be easily cleaned without preparing a cotton swab or the like immersed in alcohol.

If the specified light intensity cannot be obtained by the light receiving unit 9, the contamination can be removed once again by the cleaning unit 2, and the origin of light absorbance can be reliably set while confirming whether or not the specified light intensity can be obtained by the light receiving unit 9.

In addition, if the specified light intensity cannot be obtained by the light receiving unit 9, the contamination adhering to the light transmission unit 7 and the light receiving unit 9 can be removed just by causing ultrasonic vibration of the water W once again, without requiring movement of the light transmission unit 7 and the light receiving unit 9.

(1) In the standard device for origin of light absorbance described above, the cleaning unit 11 was configured by comprising the cleaning tank 11 and the ultrasonic transducer 12, but the standard device may also be configured by forming cotton on the side surface of the laminar body in which the polyacetal resin plate 3 and the neoprene rubber plate 4 are laminated.

Figure 6:
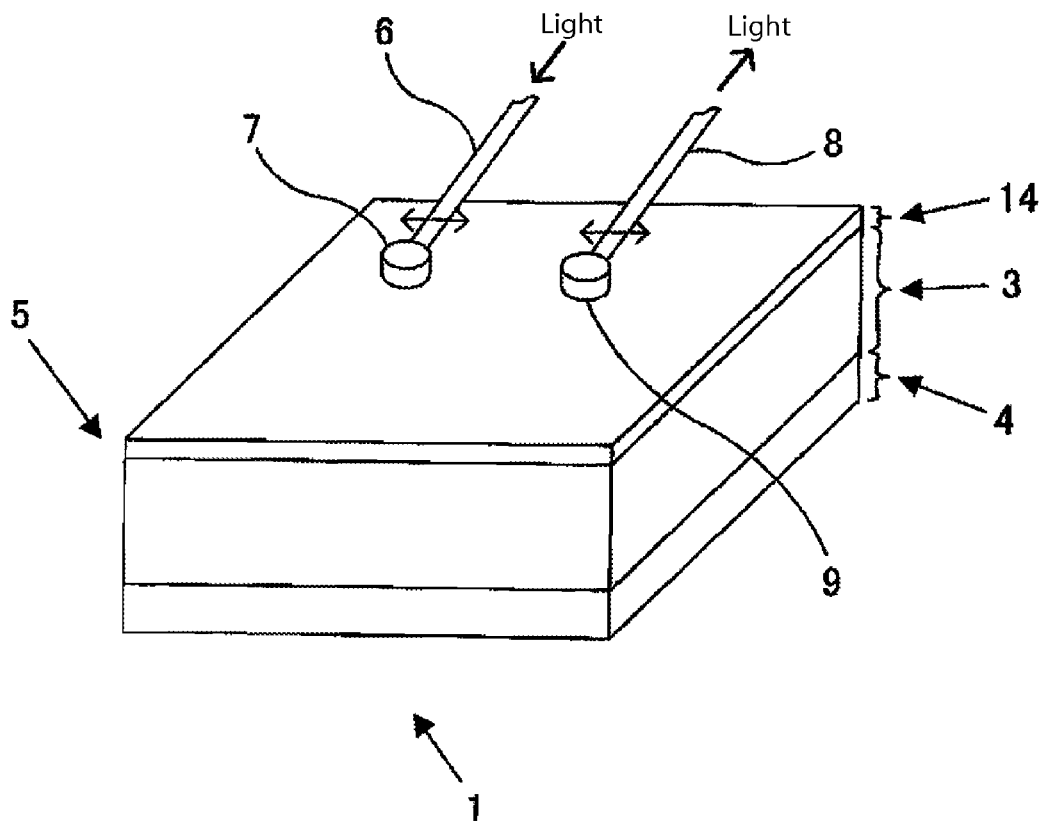
FIG. 6 is a perspective diagram indicating another example of a standard device for origin of light absorbance that is an embodiment of the present invention.

(2) FIG. 6 is a perspective diagram indicating another example of the configuration of a standard device for origin of light absorbance that is an embodiment of the present invention. Further, the same codes are used for the items that are the same as the standard device for origin of light absorbance 1 described above. As indicated in FIG. 6, the standard device for origin of light absorbance 1 is configured by mounting a fabric 14 on the surface of the polyacetal resin plate 3. According to this kind of configuration, the contamination can be removed by soaking the fabric 14 with alcohol, bringing the light transmission unit 7 and the light receiving unit 9 into contact with the surface of the fabric 14, and manually causing the light transmission unit 7 and the light receiving unit 9 to move horizontally so that they are pressed onto the surface of the fabric 14. Then, after removing the contamination, with the light transmission unit 7 and the light receiving unit 9 remaining in contact with the fabric 14, the measurement light emitted from the light transmission unit 7 enters the interior of the polyacetal resin plate 3 from the surface of the polyacetal resin plate 3, passes through the interior of the polyacetal resin plate 3, exits to the exterior of the polyacetal resin plate 3 from the polyacetal resin plate 3 and then arrives at the light receiving unit 9.

Figure 7:
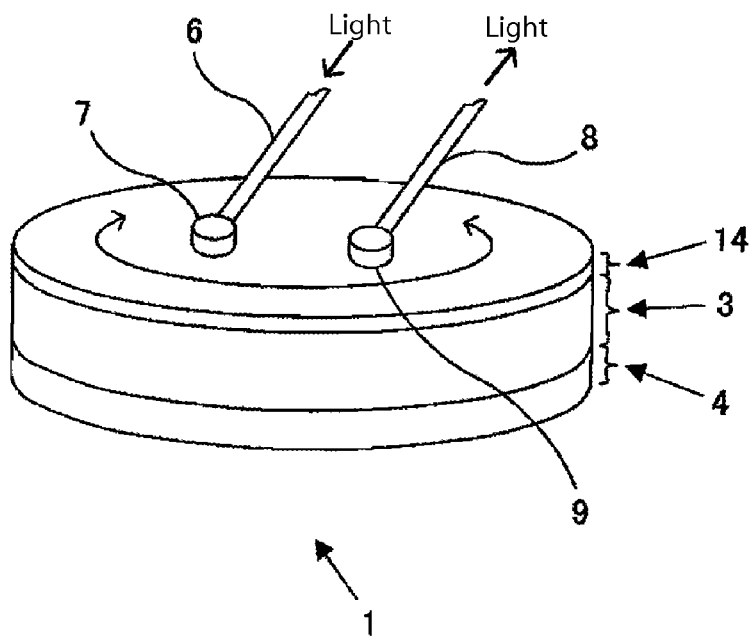
FIG. 7 a perspective diagram indicating another example of a standard device for origin of light absorbance that is an embodiment of the present invention.

(3) FIG. 7 is a perspective diagram indicating another example of a configuration of a standard device for origin of light absorbance that is an embodiment of the present invention. Further, the same codes are used for the items that are the same as the standard device for origin of light absorbance 1 described above. As indicated in FIG. 7, the standard device for origin of light absorbance 1 is configured so that the entire unit of the fabric 14, the light diffusion plate 3 and the light absorption body 4 (laminar body in the shape of a circular disk) can be manually or electrically rotated using the central axis as the center of rotation. According to this kind of configuration, after the light transmission unit 7 and the light receiving unit 9 have contacted the surface of the fabric 14, contamination between the surface of the fabric 14 and light transmission unit 7 and light receiving unit 9 can be removed by rotating the entire unit of the fabric 14, the light diffusion plate 3 and the light absorption body 4. Then, after the contamination has been removed, with the light transmission unit 7 and light receiving unit 9 remaining in contact with the fabric 14, the measurement light emitted from the light transmission unit 7 enters the interior of the polyacetal resin plate 3 from the surface of the polyacetal resin plate 3, passes through the interior of the polyacetal resin plate 3, exits to the exterior of the polyacetal resin plate 3 from the polyacetal resin plate 3 and then arrives at the light receiving unit 9.

The present invention can be used in light measuring instruments that measure the optical characteristics of light diffusion samples such as living bodies.

LEGEND

1, 20 Standard device for origin of light absorbance
2 Cleaning unit
3 Polyacetal resin plate (light diffusion plate)
7 Light transmission unit (light transmission terminal)
9 Light receiving unit (light receiving terminal)
26 Living body oxygen monitor (optical measuring instrument)

We claim:

1. An absorption standard device that provides a standard for an origin of light absorbance, comprising:
   a light diffusion plate through the interior of which a measurement light can be diffused and transmitted; and
   a cleaning unit that cleans a light transmission terminal and a light receiving terminal of an optical measuring instrument.

2. The absorption standard device for an origin of light absorbance according to claim 1 wherein the cleaning unit includes
   a cleaning tank formed by a plurality of side walls and a bottom surface, the bottom surface including the light diffusion plate,
   a cleaning solution that is contained within the cleaning tank, and
   an ultrasonic transducer that generates ultrasonic vibrations in the cleaning solution.

3. The absorption standard device for an origin of light absorbance according to claim 1 wherein the cleaning unit includes a fabric laminated on a surface of said light diffusion plate.

4. The absorption standard device for an origin of light absorbance according to claim 3 wherein the laminated fabric is rotatable relative to the light transmission terminal and the light receiving terminal.

5. A method of using a device for an origin of light absorbance used in an optical measuring instrument for measuring light absorption characteristics of a light diffusion sample, the method comprising:
   filling a cleaning tank at least partially with a cleaning solution, the cleaning tank formed by a plurality of side walls and a bottom, the bottom including a surface of a light diffusion plate;
   immersing in the cleaning solution a light transmission terminal and a light receiving terminal;
   generating ultrasonic vibrations in the cleaning solution using an ultrasonic transducer so as to remove contaminations from the light transmission terminal and the light receiving terminal;
   receiving an irradiated measurement light from the light transmission terminal at a point of incidence of the light diffusion sample and through the light diffusion plate, the light diffusion plate diffusing and transmitting the measurement light;
   producing a reflected measurement light reflected from a point of detection of the light diffusion sample, the point of detection being separate from the point of incidence; and
   measuring at said light receiving terminal the measurement light irradiated from said light transmission terminal into the interior of the light diffusion plate, through the interior of said light diffusion plate, and reflecting from and exiting to the exterior of the light diffusion plate.

6. A method of using a device for an origin of light absorbance used in an optical measuring instrument for measuring light absorption characteristics of a light diffusion sample, the method comprising:
   filling a cleaning tank with a cleaning solution, the cleaning tank formed by a plurality of side walls and a bottom, a bottom including a surface of a light diffusion plate;
   immersing in the cleaning solution a light transmission terminal and a light receiving terminal;
   generating ultrasonic vibrations in the cleaning solution using an ultrasonic transducer so as to remove contaminations from the light transmission terminal and the light receiving terminal;
   rotating a drive mechanism configured to rotate a laminar body of a fabric and a light diffusion plate;
   bringing the light transmission terminal and the light receiving terminal into contact with a fabric surface not laminated to the light diffusion plate during the rotation of the drive mechanism;
   receiving an irradiated measurement light from the light transmission terminal at a point of incidence of the light diffusion sample and through the light diffusion plate, the light diffusion plate diffusing and transmitting the measurement light;
   producing a reflected measurement light reflected from a point of detection of the light diffusion sample, the point of detection being separate from the point of incidence; and
   measuring at said light receiving terminal the measurement light irradiated from said light transmission terminal into the interior of the light diffusion plate, through the interior of said light diffusion plate, and reflecting from and exiting to the exterior of the light diffusion plate.

* * * * *